(12) United States Patent
Väisälä et al.

(10) Patent No.: US 6,377,346 B1
(45) Date of Patent: Apr. 23, 2002

(54) SAMPLE IMAGING DEVICE

(75) Inventors: Mikko Väisälä, Piikkiö; Jarmo Nurmi, Kuusisto; Jarmo Korpi, Nousiainen; Raimo Harju, Turku, all of (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 09/398,996

(22) Filed: Sep. 17, 1999

(30) Foreign Application Priority Data

Sep. 17, 1998 (FI) .................................................. 982005

(51) Int. Cl.⁷ .............................................. G01N 21/27
(52) U.S. Cl. ..................................... 356/417; 250/458.1
(58) Field of Search ................................. 356/317, 318, 356/417, 23; 250/458.1, 459.1, 461.1, 461.2

(56) References Cited

U.S. PATENT DOCUMENTS

| | | | | |
|---|---|---|---|---|
| 4,566,797 A | * | 1/1986 | Kaffka et al. | 356/402 |
| 4,782,386 A | * | 11/1988 | Ams et al. | 356/23 |
| 6,236,457 B1 | * | 5/2001 | Allen et al. | 356/328 |

* cited by examiner

Primary Examiner—Richard A. Rosenberger
(74) Attorney, Agent, or Firm—Kubovcik & Kubovcik

(57) ABSTRACT

An imaging device for biochemical or medical samples, the pulse mode light source of which incorporates flash lamps and a rotating mirror in an inclined position, the said mirror reflecting the light emitted by each flash lamp in turn along the same optical path to the sample. The flash lamps are switched on alternately in phases and synchronised with the rotating mirror and the emission light chopper, which comprises two rotating discs. The turning mirror directs the light at the sample from above and/or below, in which case a double-acting transparent scattering plate can be used.

22 Claims, 10 Drawing Sheets

SAMPLE IMAGING DEVICE

OBJECT OF THE INVENTION

The object of the present invention is a system for measuring biochemical and medical samples, the said measuring being carried out by imaging. The objects of imaging are mainly regular macro-size sample matrices, gels, Petri dishes or completely free-form samples, such as, for example, biological sections. The signal to be imaged is ultraviolet light, visible region light, or infrared light.

Light-producing mechanisms are:
1) luminescence, such as chemiluminescence and bioluminescence, in which case the light p produced by each sample at different points of the sample is measured,
2) fluorescence, in which case the amount of emission light produced by special excitation light at different points of the sample is measured ed, and in addition
3) the amount of reflection, scattering, or absorption at different points of the sample, resulting from the illumination of the sample.

PRIOR ART

In known measuring devices many different types of sample plates are used, in which the number of wells may vary considerably. In a conventional sample plate there are, for example, 96 sample wells, in which case the amount of solution required for each well is 200 $\mu$l. Another typical number of wells is 384 wells in a sample plate, in which case the amount of the solution required for each well is, for example, 200 $\mu$l. Although these amounts are small as such, in cases where, for example, 100 000 samples are measured during one sample run, the overall costs are considerable. It obviously makes a marked difference whether 50 $\mu$l of liquid or 1 $\mu$l of the same liquid is used for one sample, which may, for example, be a single patient sample. The costs relating to the consumption of liquid are directly proportional to the volume used. In the course of measurements, during one set of sample measurements, that is, a sample run, considerable amounts, i.e. several litres of used solution is produced, the said solution often being hazardous waste. The residues of solution often contain radioactive and/or toxic chemical compounds. When numerous sample runs are performed daily (on parallel equipment and in different laboratories), the amount of toxic solution waste produced is considerable. Thus there are obvious reasons to reduce the amounts of solution significantly, that is, in practice to reduce the sample well volume.

To reduce the amount of liquid and to speed up measurements, sample plates with 864 wells are now being used in several measuring devices, in which case the amount of solution required is, for example, about 10 $\mu$l. The aim has, however, been to reduce the size of the wells even further. There now already exist sample plates with 1536 wells in which the amount of solution required is now only 5–10 $\mu$l, and possibly even as little as 1 $\mu$l. In the near future the number of wells will increase further—sample plates with e.g. 9600 wells are being tested in laboratories.

Reducing the size of the sample wells has, however, caused problems, because a small-volume sample requires much better and more efficient measuring properties of the measuring device. Known devices do not usually meet these requirements without extremely complex constructions, or else their measuring times are unacceptably long, which affects the reliability of the measuring results and which also makes the use of parallel equipment compulsory in order to obtain a reasonable overall measuring time for the set of samples.

In luminescence and fluorescence measurements, the aim of reducing the volumes of the wells results in the amount of light from the sample well decreasing in proportion to the volume of the well. In luminescence measurements this means that either the measuring time must be extended correspondingly, or more sensitive measuring devices than the conventional ones have to be used. In fluorescence measurements the situation is different; the amount of fluorescent light produced is proportional to the efficiency, that is, intensity of the light of the excitation light. Especially when operating within the linear range of fluorescence, where the yield of emission light is directly proportional to the amount of excitation light, by doubling the intensity of the excitation light, for example, the amount of the emission signal obtained from the sample, that is, the amount of fluorescent light from the sample will also be double. In a measuring situation such as this it is obvious that the aim will be to increase the intensity of the excitation light considerably, so that shorter measuring times can be used.

In traditional fluorometry, one sample well is measured at a time. In such a case, the excitation light originating, for example, from a xenon flash lamp, is directed by means of focusing optics directly at the sample solution contained in one sample well. Each sample well is measured separately and in the same manner as the previous one.

In imaging, however, the situation is completely different. In this case, where the aim is to image all sample wells at the same time, the excitation light is directed at all the wells simultaneously. The easiest way to do this is by illuminating the entire sample plate with excitation light at one time. However, as the size of the sample plate may, for example, be 80 mm×120 mm, and the surface area of one well in a single plate comprising 1536 wells may be 1.5 mm×1.5 mm, it is obvious that in order for the imaging to be successful, considerably more excitation light is required for imaging than for fluorometry, if the measuring times are to be of the same magnitude.

From this it follows that in fluorescence measurement it is difficult to obtain sufficiently powerful excitation light in the sample plate area, that is, in each sample well. It is also desirable that the uniformity of the excitation light field, that is, its intensity distribution over different parts of the sample plate should be as uniform as possible. The overall sensitivity of the measurement, that is, how small a specific part of a sample will be detected, is determined by that point in the excitation field which has the lowest intensity.

A continuous light source, for example, an arc lamp or a halogen lamp or any other device generating light continuously, is sufficient for prompt fluorescence. However, for time-resolved fluorescence a pulse mode light source is required, for example, a flash lamp or a pulsed laser. The length of the light pulse is of decisive importance for the sensitivity of the device, a property which in turn depends on the decay time of the fluorescence in the sample.

A pulse mode light source may be one of the following:
a) a flash lamp
b) a pulsed laser, such as the combination of an XeCl excimer laser and a dye laser or, for example, a nitrogen laser
c) a combination of a continuous light source and a light chopper; continuous lamps include an arc lamp, a halogen lamp, a continuous laser, and other lamps that produce light continuously.

For example, the light of an arc lamp is interrupted by means of a light chopper in the excitation/illumination path. In practice, the operation of this type of combination is rather ineffective, depending, however, on the application.

Time-resolved fluorescence is achieved by using a combination in which the light source is a pulse mode lamp and the camera acting as detector can be gated. The gating of the camera is a rapid shutter function. This is required because the illumination path leading to the camera must be shut at the moment when the light source flashes. It is only after this that the illumination path of the camera is opened. In practice, the gating of the camera can be done mainly by means of the following combinations of devices:

a) a sensitive camera, in front of which is a mechanical light chopper,
b) a sensitive camera, in front of which is a liquid crystal shutter device, which is triple if necessary.
c) an intensified charge coupled device camera
d) a gatable camera In prompt fluorescence, it is possible to use a powerful lamp, because it applies spectral filtering. Excitation light and fluorescent light, which are at different wavelengths, can be separated from each other by means of a spectral filter. A disadvantage of prompt fluorescence is, however, that prompt fluorescence also easily comes from other fluorescent parts of the sample than from the fluorescent tracer being measured. This type of fluorescence at another point typically emits light over a wide wavelength region, which means that it is also emitted in the emission wavelength of the fluorescent tracer being measured. Since the optical filter in front of the camera has been selected according to the wavelength of the tracer, prompt fluorescent light originating from another single point than the tracer being measured can also enter the camera. In the image, these points may overlap, which sometimes makes it impossible to say, when analysing and observing the image, whether the signal comes from the fluorescent tracer being measured or from other interfering fluorescent light in the sample, which causes a background signal. Another disadvantage of prompt fluorescent imaging is that excitation light may also enter the camera, which causes more interfering background signals, which further reduces the measuring sensitivity of the measurement, that is, imaging.

In the imaging device relating to the invention, which does not apply time-resolved imaging as in prompt fluorescence and luminescence imaging (another embodiment), there is a dimmer in place of the chopper 13. In this case the optics also incorporate a mechanical shutter controlled electrically, pneumatically or otherwise, or a liquid crystal shutter device to shut the illumination path leading to the camera before the imaging signal is read electrically on the ccd matrix of the camera, which signal is formed into a digital image.

For imaging time-resolved fluorescence, a light chopper is needed in front of the detector, that is, in this case a sensitive, cooled ccd camera, by means of which the emission light path is interrupted for the short interval during which a short fluorescent excitation light pulse originating from a pulse mode light source is directed at the sample. After this the light chopper opens the illumination path leading to the camera to allow the passage of the long-living fluorescent light emitted from the sample to the camera. The chopper may, for example, be a mechanical rotating light chopper or a liquid crystal shutter device (LCD), which is most preferably located on the aperture plane of the imaging optics, which means that light chopping takes place in a controlled manner, without disturbing shadows or dark areas or other irregularities attributable lighting, being formed in the image.

If a separate light chopper is not used, time-resolved imaging can be performed by using an Intensified Charge Coupled Device (ICCD) camera.

It has been shown in practice that time-resolved (TR) fluorescence measurement is advantageous in many respects. If sufficiently short and powerful excitation light intensity is obtained for the sample in this measurement, there will also be sufficient time for measuring fluorescence after the excitation light has been switched off. However, for the above reasons, the reduced size of the sample wells and the increased number of wells have caused problems.

It is difficult to obtain uniform and sufficiently powerful excitation lighting over the entire sample plate area. At the same time, the exposure time should nevertheless be short enough to enable efficient measurement immediately after the excitation light has switched off. Long measuring times are unacceptable because in such a case the measuring device is too ineffective in practice.

Increasing the power of the excitation lamp has not provided a solution to this problem, because the pulse length of a powerful lamp is relatively long, for example, about 300 ps. The excitation fluorescence of many fluorescence measuring agents is halved already about 200 $\mu$s after excitation, and thus the fluorescent light is covered under the excitation light.

Differences between cameras

1. Cooled CCD camera, that is, c-CCD (=cooled Charge Coupled Device): good resolution, wide dynamic range, good sensitivity, difficult to gate
2. Intensified Charge Coupled Device or ICCD camera: limited resolution, limited dynamics, good sensitivity, easy to gate.

The lens systems used in connection with excitation light sources also cause problems when the size of sample wells is reduced. Normally, the light emitted from the lens disperses so that the beams of light enter the sample well at an oblique angle, which means that the sample wells in the centre of the sample plate are obviously illuminated in a different manner than the sample wells at the edges of the sample plate.

The efficiency of measurement is also impaired by the fact that as the number of sample wells increases, the intermediate walls of the sample wells make up an increased relative proportion of the sample plate surface area. From this follows that the sample fluid in the sample well obtains too small a proportion of the excitation light. To achieve uniform and sufficiently intensive excitation lighting, the light beams must enter the sample well at a sufficiently small angle. According to one embodiment, a small entry angle of the excitation light beams is obtained by positioning the light source sufficiently far away from the sample.

Imaging lens systems

The question here is, therefore, of imaging at a fairly considerable downscaling-ratio, that is, about 1:5, because the size of the sample plate is about 80×120 mm and the size of the ccd matrix is, for example, 25×17 mm with current technology. It is easy to calculate the above-mentioned downscaling ratio on the basis of these figures. It would be more advantageous if the downscaling required for imaging were not so great, but closer, for example, to the ratio 1:2. However, ccd matrices are not widely available commercially in other than the above magnitude. It is, however, likely that the situation will change in the near future, which means that imaging will become more efficient from the point of view of measuring technique.

When imaging a sample, an image of the sample is formed on the camera on the basis of the emission light (luminescence, fluorescence, absorbancy) emitted by the sample. When using conventional optics such as a conventional objective camera lens, the parallax error of imaging is considerable due to the downscaling ratio used. In such a case the edges of the sample plate are imaged much less effectively than the sample wells in the centre of the plate. In order to be able to eliminate this drawback and to maximize the collection of light, a telecentric lens system should be used in imaging. In this case the sample wells in the centre and edges of the sample plate are imaged with equal efficiency.

According to a dictionary of optics, a telecentric lens is: "a lens in which the aperture stop is located at the front focus, resulting in the chief rays being parallel to the optical axis in the image space, i.e. the exit pupil is at infinity" (The Photonics Dictionary, 1993: Telecentric Lens).

For reasons relating to the basics of optical design, the lens system which collects light from the sample plate area must be designed so that at least two types of glass with different refractive indices are used. Moreover, good resolution is required of the optics, since the sample wells are imaged in small size on the camera. This means that the telecentric lens system has, for example, about 20 separate lens elements or even more.

From this it follows in turn that the total transmittance of the lens system is limited mainly to the visible area, that is, the wavelength 400–800 nm. In order to be able to utilize the total transmittance of the said lens system, the lens elements must in practice be coated with Anti Reflex coating film (AR-coating). If the said AR-coating films were not used, total transmittance would remain rather low.

KNOWN AREAS OF APPLICATION

In the HTS method, the use of fluorescent label molecules is restricted by the large number of samples; measurement results remain unreliable when using fluorometers because with large numbers of samples the output of the excitation lamps decreases, resulting in the need to service instruments even during operation. If, however, a combination consisting of several flash lamps is used, the lamp unit will be sufficiently powerful and the intervals for changing the lamp bulbs will be sufficiently long.

AIM OF THE INVENTION

The aim of the invention is to achieve a versatile and efficient imaging device for luminescence, prompt fluorescence, time-resolved fluorescence, and absorbancy, that is, as for transmittance and photometric measurements.

The aim is to carry out mainly the following types of measurements with the device relating to the invention:

1. Prompt fluorescence
2. Time-resolved fluorescence (TR fluorescence)
3. Fluorescence polarization
4. Luminescence, such as chemiluminescence and electroluminescence
5. Absorbancy
6. SPA (=Scintillation Proximity Assay)

ADVANTAGES OF THE DEVICE RELATING TO THE INVENTION

The present imaging device provides a solution to the problem of how to realize a sufficiently powerful lamp unit which produces a sufficiently short light pulse. This type of unit comprising several flash lamps is the only possible lamp for many time-resolved fluorescence measurements. One example of these is homogeneous fluorescence assay LANCE, which is a trademark of Wallac Oy. No such powerful lamp is known with which measurement can take place within a sufficiently short measuring time. The measuring time should be short, e.g. 2 minutes, in order for the total measuring time in High Throughput Screening to be acceptable. The total number of samples in one HTS run may be, for example, 100 000 samples, that is, sample wells. Measuring such a large number of sample wells by traditional fluorometric means would take an extremely long time. The amount of hazardous waste produced would also be considerably higher. A combination of a powerful pulsed laser and a dye laser could in principle be used, but it is an unnecessarily complex and uneconomical device which is also difficult to service.

The intervals for changing the lamp bulbs of the light source become extremely long when a lamp combination consisting of flash lamps is used. This is of considerable importance in HTS runs where the aim is to minimize the number of stoppages. When using conventional continuous, that is, continuous wave lamp units, for example, mercury or xenon arc lamps or halogen lamps, the lamp changing intervals are without exception too short considering the demands of HTS screening. One of the few possible solutions when using continuous lamps would be that the lamp could be changed automatically, but it is rather difficult to arrange this to function reliably.

The device relating to the invention combines the absorption measurements of both the near ultraviolet region and of visible light, or, vice versa, transmittance measurements, that is, in practice photometric measurements: the absorption of near UV is required especially in the applicant's LANCE measurements. Absorption measurements in the visible region are in the nature of standards in terms of measuring technique.

The difficulties in using both absorption modes, such as near UV and visible region light mainly concern optics. It is almost impossible, or extremely uneconomical, to construct a telecentric lens with such a high light-collecting efficiency that would transmit effectively the wavelengths of both near UV and visible region light. Typically, a lens system which collects light efficiently and has good resolution can be made either in the near UV region, or alternatively in the wavelengths of visible light. This means that typically only absorption imaging in the visible region or absorption in the near UV light region are possible. In the application relating to the invention, on the other hand, a special scattering plate is used by means of which both near UV and visible light absorption measurements can be imaged.

The light source solution relating to the invention is advantageous for measuring numerous samples done by imaging, for example, especially in demanding applications such as HTS screening and both time-resolved and prompt fluorescence measurements. The device is able to image absorption measurements efficiently both in the near UV light region, that is, in 300–400 nm, and in the visible region, that is, 400–800 nm.

The size of a commonly used sample plate is 120×80 mm, which is imaged at one time, and a digital image is produced from it. In the example device, a sample area as large as 240×160 mm can be imaged in four parts one after another. The four images obtained in this way are combined into one by means of software. The sample may otherwise be of any shape, so long as it meets the boundary dimensions of the example situation. The amount of light produced by the sample and the desired resolution of details are decisive as regards the imaging efficiency of the device. The thickness chosen for the sample in this case equals plate thicknesses within the range of 0 . . . 30 mm.

In the device relating to the invention there are the following possible ways of illuminating or exciting the sample:

1. The sample can be illuminated and/or excited from above and/or below.
2. The sample can be imaged from above or below.

For measuring (imaging) the sample plate from below, the device is turned upside down.

Properties of the illumination system relating to the invention:

1. High average total pulse power
2. Narrow pulse width, which is required in the embodiment used as an example
3. The use of several lamps makes it possible to select the pulse energy of a single lamp so that the fluorescent sample will not become saturated. If a single lamp with high pulse power were used, the sample might become saturated, which would mean a sharp drop in the sensitivity of detection.
4. The use of several lamps also means that even if there should occur a fault in a single lamp, the overall efficiency remains almost unchanged in proportion to the number of lamps.
5. Using several pulse mode lamps also means that the intervals for changing the lamps are extremely long, for example, about six months. This is due to the fact that a pulse mode lamp is switched on only when it is really used. There is no wastage.

If, for example, a continuous arc lamp is used instead, the lamp will have to be changed at least at one month intervals. This is due to the fact that a continuous lamp is switched on all the time, that is, also when there is no sample in the sample space. It is not worthwhile, nor possible, to switch a continuous lamp off for example for a 15 minute waiting period, because the lamp reignites slowly due to the increase in the internal gas pressure inside the lamp, which is due to the warming up of the lamp following its use, this making it difficult, or even impossible, to reignite the lamp . In addition, stabilizing the arc lamp, that is, stabilizing its power within a desired wavelength region cannot be performed successfully if the lamp is switched on and off, for example, at 15 minute intervals.

A powerful light source is required in order for fluorescence measurement to be efficient. According to one embodiment, sufficiently strong excitation light is produced by using several lamps for the illumination, which can be switched on either simultaneously or successively by phasing.

If the lamps are switched on simultaneously, the simplest way is to position all the lamps in such a way that they can be directed towards the centre of the sample plate, and arrange the travel of the light beams by means of lenses so that the illuminating beams emitted from the lamps are distributed evenly across the entire sample plate from each lamp separately, but at the same time.

According to one embodiment, the lamps are situated on the circumference of a circle and their light is directed towards the centre of the circle, where there is a polygon mirror. In the polygon, there is an individual reflection plane for each lamp, the said plane reflecting the light beams of the lamp towards the centre of the sample plate. By means of the lenses, the light is distributed evenly over the entire sample plate area.

If the lamps are switched on successively by phasing, according to one embodiment the lamps are also situated on the circumference of a circle and their light is directed towards a rotating, for example, ellipse-shaped mirror in the centre of the circle. The rotating mirror is in an inclined position, for example, at a 45 degree angle, so that when the mirror rotates, it reflects the light from each flash lamp in turn onto the sample plate, preferably along the same optical path. This is implemented by triggering each flash lamp at the precise moment when the rotating mirror is in such a position during its movement that the illuminating beam emitted from the flash lamp at the moment of triggering strikes the reflecting surface of the rotating mirror so that the light beams are directed further towards the sample plate. The speed of rotation of the rotating mirror should not be too high, so that the random time lag resulting from the minor natural inaccuracy of the triggering moment between the triggering event and the flash of light from the lamp will not hinder the travel of the light beams in the desired optical path towards the sample plate. While the mirror is still rotating towards the next flash lamp, this lamp is being triggered in the same manner as the previous lamp and the light beams from this next lamp are directed in the same manner as above towards the sample plate. This function takes place at each individual flash lamp while the mirror is still rotating, with the result that during one full rotation of the rotating mirror, each flash lamp is triggered once, that is, each of the lamps has flashed once at precisely the appropriate moment, which corresponds to that point on the rotational angle of the mirror at each individual lamp, where the light beams are directed towards the sample plate.

The function described above only succeeds when pulse mode light sources are used which can be triggered. In such a case each flash lamp is controlled at full power which means for each individual lamp that the electric pulse fed to each individual lamp is exactly as high as the frequency complying with the rotation of the rotating mirror, that is, as high as the frequency, or cycle time, allows for each individual lamp. For example, if the speed of rotation of the rotating mirror is 6000 rpm (roots per minute), that is, one rotation lasts for 10 milliseconds, and if a lamp unit using, for example, eight flash lamps is used as a light source, in that case each of the eight lamps is triggered at 10 millisecond intervals, each at the precise moment when the rotating mirror is at the individual lamp in question. Since each individual lamp is triggered at 10 ms intervals, this means that each lamp is triggered 100 times per second, that is, at a frequency of 100 Hz. In the device application relating to the example a flash lamp with a maximum permitted average power of 50 watts (W) is used. In such a case, when the lamp is used at a frequency of 100 Hz, this means that 0.5 joules of energy is supplied to the lamp at each triggering. The said amount of energy is thus supplied to each lamp separately at the precise moment which corresponds to that point on the rotational angle of the rotating mirror at which it is at the individual lamp. Thus, in this example, each individual lamp is supplied with 100 Hz, that is, at intervals of 10 milliseconds, 0.5 joules energy is supplied to each lamp, which corresponds to an average power of 50 watts per each lamp separately. From this follows that the overall output of the lamp system as a whole is on average eight times 50 watts, that is, 400 watts. The overall output is, therefore, directly dependent on the total number of lamps.

In practice this means that each lamp is controlled, or triggered, with the highest average power permitted, that is, with 50 W. Due to the movement of the rotating mirror, each of the eight lamps in the lamp unit can be used at the full power permitted. In this way an average power output of 400 watts is produced by the system of eight lamps relating to the example.

The length of the pulse of a flash lamp is mainly only about 1 microsecond. However, the light pulse has a "tail" extending up to about 50 microseconds, the said tail limiting the sensitivity of measurements when the aim is to achieve extreme sensitivity. The operation of the flash lamp can be made more efficient by incorporating a so-called "tail light chopper" in the lamp unit. In that case each excitation light pulse should be shortened by positioning a device which functions like a fast shutter in front of the lamp, in order to cut off the excitation illumination path after each excitation light pulse. Thus, if the operation of this type of chopper were rapid enough, the light tail of the lamp could be cut, for example, 3 μs after the moment of triggering the lamp, and in this way the flash lamp would produce an excitation light pulse lasting at longest 3 ps in total, which would extend the scope of application of the said lamp.

When measuring the fluorescent homogeneous sample referred to in the invention, it is sufficient if, for example, the light tail of the lamp is cut off about 30 μs from the moment of triggering the lamp.

The tail light chopper can be implemented in several ways. Its operation can be combined with the operation of the rotating mirror, in such a way that if the rotating mirror rotates fast enough, due to this movement of the mirror, the tail of the light pulse is cut off timewise as the rotating mirror rotates further towards the location of the next lamp. In time-resolved measurements it is also important that enough time remains after excitation for measuring the emission signal before the next excitation pulse is directed at the sample. The rotating mirror can be rotated faster, in which case the cutting of the light tail becomes more accurate. In such a case it may, however, be more advantageous if the next lamp being triggered is the one after the next (in other words, every other lamp in the lamp system is triggered), in order to utilize the emission light of the fluorescence in an efficient manner. In this case there should preferably be an odd number of lamps in the lamp system, so as to make use of all the lamps. If there is an even number of lamps in the unit and the type of lamp triggering method described is to be used, care should be taken that the even number of lamps to be triggered is alternated at regular intervals. The selection can be automated by means of an electric coupling. This means that in a system comprising eight lamps, four lamps (such as, for example, lamps 1, 3, 5 and 7) are triggered first, and then after a regular interval, the remaining four lamps (that is, lamps 2, 4, 6 and 8 would be due to be triggered). When the group of lamps to be triggered is changed at regular intervals, all the lamps are used up evenly.

The structure of the lamp unit is not limited by the requirement of having an even or odd number of lamps.

The lamps in the lamp unit can also be triggered in other ways. The order of triggering can in itself be selected freely, because the selection is done by means of an electric circuit coupling or the program command of a computer processor, or a combination of these, and because this may give the advantage that the method of use, or the point of operation of an individual lamp can be made more appropriate considering, for example, the lamp's service life or its UV light production, than by triggering the said lamps in strict order as described above.

Structurally, the tail light chopper may also be a separate mechanical light chopper which is located after the lamp so that the length of the aperture or the lengths and shapes of the apertures in it determine the true length of the light pulse. This type of tail light chopper is timed, that is, synchronized with an emission light chopper and the rotating mirror situated in the lamp unit, so that these operate together in a synchronous manner.

It is not worth using the rotating mirror system if continuous light sources are used as lamps. This is simply due to the fact that when the mirror rotates, and when each lamp is switched on all the time (because in such a case it would be a question of using continuous wave lamps, that is, continuous lamps), every time that the mirror is not exactly at the individual lamp, the optical power will be directed past the mirror most of the time, and thus not at the sample. On the other hand, if a fixed mirror polyhedron was to be used instead of the rotating mirror, in such a case both pulse mode and continuous light sources could be used. In that case the overall service life of the continuous light sources would naturally also depend on the number of lamps in the system, because whenever the service life of one continuous lamp came to an end, a new lamp would be switched on and operation could continue uninterrupted while the lamp was being changed.

The mechanical light chopper in front of the camera and on the emission light path must be synchronized with the movement of the rotating mirror in the lamp unit. The rotating mirror and the emission light chopper will then always at a certain phase rotate with respect to each other. Phase locking is performed electronically by means of the synchronizing pulses obtained from the emission light chopper and the rotating mirror. The synchronizing pulses are obtained from opto-electronic readers, or so-called N-coders, which rotate with the emission light chopper and the rotating mirror. If a tail light chopper is in addition used in front of the lamp, this also gives synchronizing pulses according to which the electronic unit guides the operation of the rotating means in a controlled manner.

In the solution described, the sensitivity of luminescence has been maximized, taking into account the requirements of structural simplicity. The result is affected by the structures of the large and small telecentric lenses, their coatings and the properties of the camera. For the duration of luminescence measurement, the mirrors in the mirror unit 22 are moved away so as not to obstruct the illumination path leading to the detector 11, and the filter wheel containing filters which is in the filter unit 12 is moved into such a position that there are either no filters in it or else there is a special luminescence filter. The rotating discs of the light chopper 13 are moved by means of the motors rotating the discs and the electric circuit coupling controlling the motors, into such a position that the illumination path leading to the detector 11 is unobstructed.

LIST OF FIGURES

The invention is described in the following by means of examples, with reference to the appended drawings in which FIG. 1 shows the device relating to the invention diagrammatically, as seen from the side.

FIG. 2 corresponds to FIG. 1 and shows a second embodiment of the device.

FIG. 3 shows diagrammatically the shutter of the device shown in FIG. 1.

FIG. 4 corresponds to FIG. 3 and shows the shutter in another position.

FIG. 5 shows diagrammatically the light source of the device shown in FIG. 1, as seen from above.

FIG. 6 shows the light source shown in FIG. 5 as seen from another direction.

FIG. 7 shows a diagrammatic section of the sample well.

FIG. 8 corresponds to FIG. 7 and shows the sample well in another situation.

FIG. 9 shows a diagrammatic side view of the excitation illumination of the sample plate so that the travel of the light beams emitted from one individual lamp is shown schematically.

FIG. 10 shows a diagrammatic side view of a second embodiment of the excitation light system where there is a fixed, stationary mirror polyhedron in place of the rotating mirror.

FIG. 11 shows a detail of FIG. 10.

FIG. 12 shows the mirror unit of the excitation light source shown in FIGS. 10 and 11.

FIG. 13 shows a third embodiment of the excitation light system, which is simple, but not as compact as a system which uses a solid dividing mirror.

FIG. 14 shows diagrammatically the principle of measuring fluorescence.

FIG. 15 shows diagrammatically an excitation and measuring principle.

FIG. 16 shows diagrammatically an excitation illumination principle.

FIG. 17 shows diagrammatically another measuring principle.

Figure 1:
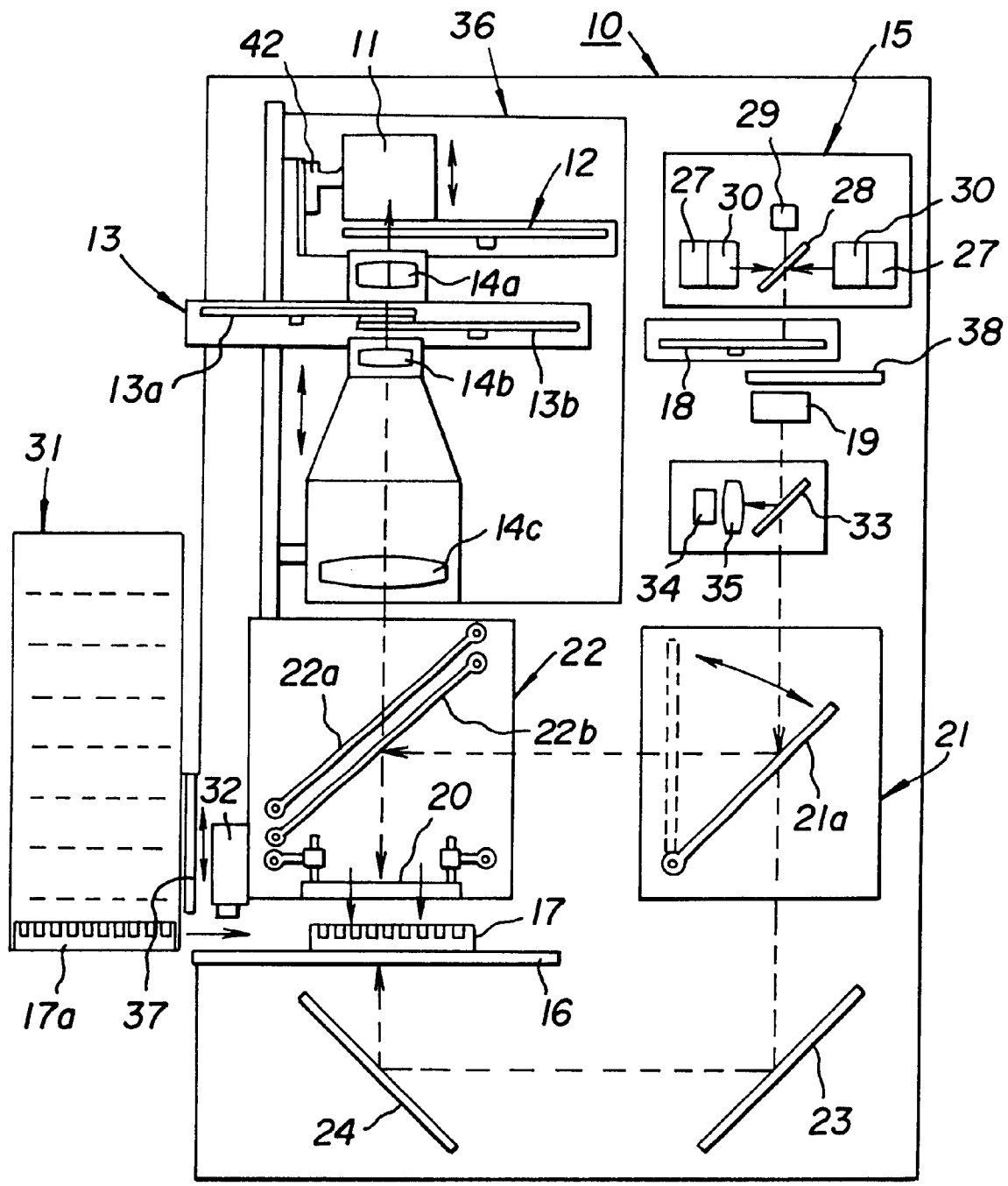
FIG. 1 shows a measuring device according to one embodiment for measuring, or in this context for imaging, different types of samples, such as, for example, fluorescent homogeneous assays. The measuring device 10 includes a detector 11, an emission filter wheel 12 in conjunction with the detector, and a set of objective lenses for emission 14. The emission objective 14 is comprised of sets of telecentric lenses 14ab and 14c. The set of lenses 14ab comprises two separate sets of lenses 14a and 14b.

The lens groups 14a and 14b of the set of lenses 14ab are situated on either side of the light chopper 13. Between the lens groups 14a and 14b is located the optical aperture plane on which the light chopper 13 is situated. The imaging unit 36 includes a detector 11, filters 12, a light chopper 13 and sets of telecentric lenses 14ab and 14c. This imaging unit can be moved in the vertical direction to make focusing on samples of different heights possible. The camera 11 also incorporates a vertical fine adjustment movement 42 for fine adjustment of focusing. This is required when the emission filter is changed, because the light wavelength region to be imaged usually also changes, which means that the image of the object forms at a slightly different distance from the object in each wavelength region.

The filter wheel 12 can also be replaced by individual filters which are located in a slide or a separate filter storage unit. This unit may, for example, have shelves for different filters and a lift or other type of filter changing apparatus, which fetches and puts the desired filter into place in the measuring device, if required.

The measuring device 10 comprises a light source 15 with several flash lamps 27 and condensing lenses 30 in front of them. The light from the flash lamps 27 is taken via the excitation light filter wheel 18 to the excitation light objective 19 by means of a rotating mirror 28. The wavelength region of the light emitted by the flash lamps 27 is so wide that the desired light wavelength band, which may be either a UV band or a visible region band, can be supplied to the sample by means of the excitation light filter wheel 18. The desired band width is selected by means of a filter. Should polarized light be required in the measurement for exciting or illuminating the sample, the filter wheel also incorporates a polarization filter, either as a separate filter or combined (simultaneously) with a band filter.

In the excitation illumination path there is also a partly reflecting mirror (e.g. 0.2% reflecting mirror) 33, which reflects a small proportion of the light through a lens 35 to a feedback photodiode 34. Also, should it be desirable to increase the efficiency of lamps' operation, a tail light chopper 38 can be used.

The measuring device 10 also includes mirror units 21 and 22, fixed mirrors 23 and 24 and, above the sample 17, a double-acting transparent scattering plate 20 for absorption measurement of both visible light and UV light.

The mirror unit 21 is an optical path switch, the mirror 21a of which is hinged and can thus be turned in front of the optical path of the excitation light, to an angle of 45 degrees. This causes the excitation light to be directed to the sample plate from above via the mirror unit 22.

The mirror unit 22 comprises a dichroic mirror 22a and a half-transmitting mirror 22b, which are located in slides so that they can optionally be moved to the illumination path or away from it. The scattering plate is also located in the slide, and can thus be brought into use when necessary. The scattering plate 20 can also be moved vertically in order to press it against the sample plate 17.

In the visible light region, absorption takes place in the sample when the sample is illuminated from below. The scattering plate 20 acts as a scattering plate, which means that an image of the light that passes through the sample is formed on the plate.

Since the lens system of a typical imaging device does not transmit UV light beams well due to the type of glass and the coatings, in the device relating to the invention the scattering plate 20 is double-acting. The plate acts as a fluorescent light wavelength converter plate in absorption measurements in the UV region, which means that visible light is obtained on the detector. Absorption of UV light takes place in the sample, which means that the UV light which is able to pass through the sample to the converter plate is indirectly proportional to the absorption taking place at different points of the sample. The intensity of fluorescent light is directly proportional to the intensity of the UV light that has passed through.

Alternatively, the scattering plate 20 used in the visible light region is replaced by a separate fluorescent converter plate when UV absorption is to be measured.

The sample table 16 of the measuring device 10 can be moved in both the x and y directions in the plane of the sample, so that any sample 17 can be moved to the detector 11 for assay. For movement in the direction of the z axis, the detector 11 is equipped with a height adjustment means. The structure of the adjustment means is not shown in FIG. 1. The sample plates are located in the storage unit 31, from where the desired sample plate 17a can be transferred to the measuring device for measurement. The bar code reader 32 identifies the sample plates 17 to be transferred to the sample table of the measuring device 10. When the sample plate has been moved in the xy direction to the detector 11, the light shutter 37 closes, which means that the measuring device is light-tight.

Figure 2:
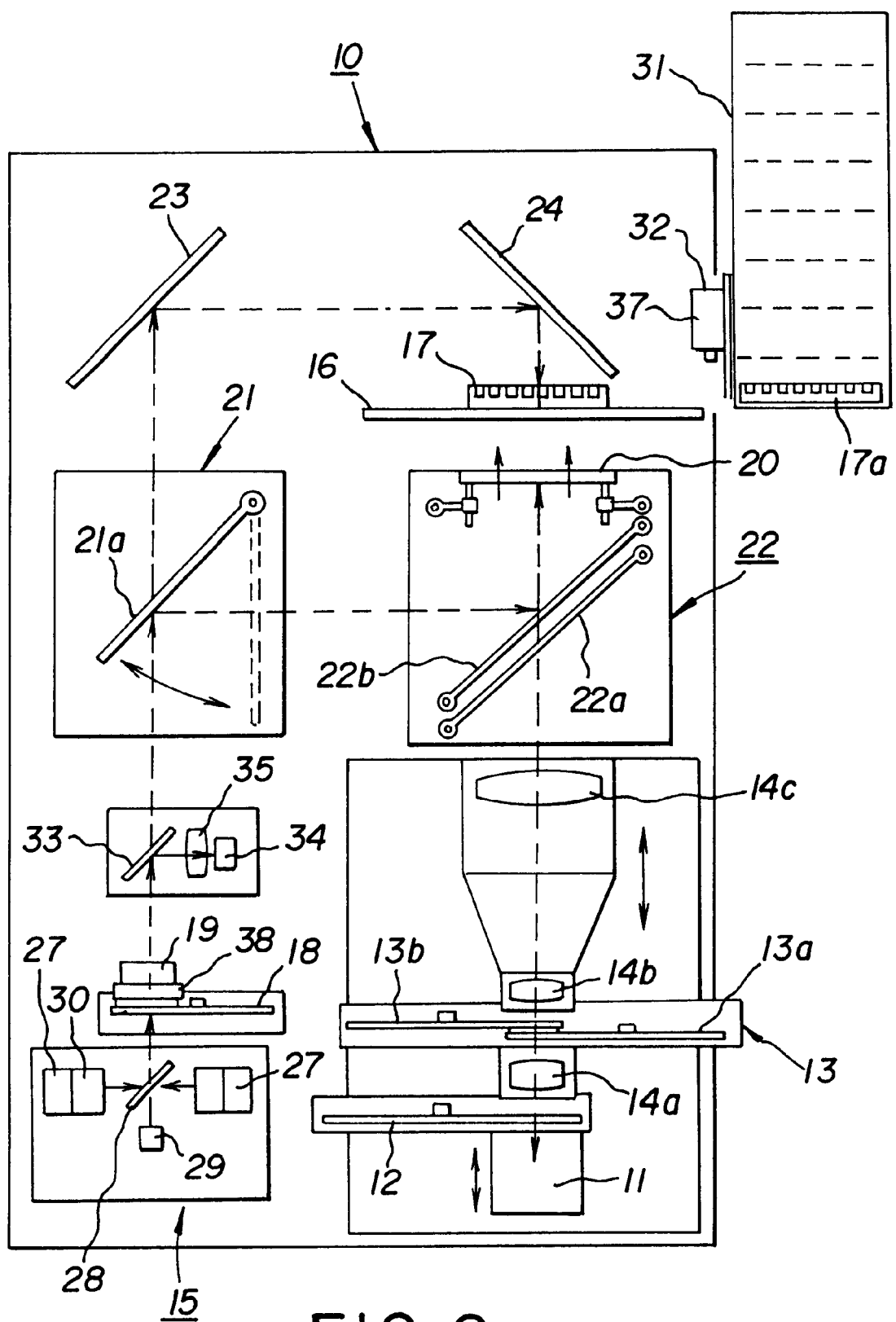

In FIG. 2, the device in FIG. 1 is shown upside down. All the measuring methods described above are possible with this device. This means that the pipetting of the sample can advantageously be carried out from above, for example, in flash luminescence measurement (which requires almost real-time pipetting) and/or the excitation of the luminescence of the sample by means of electrodes in electroluminescence measurement.

Figure 3:
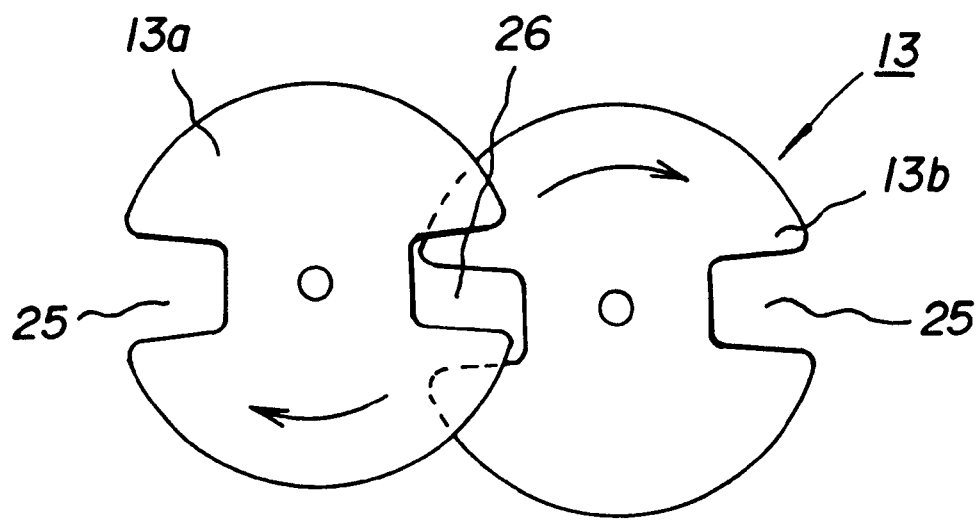

FIG. 3 shows diagrammatically the structure of the chopper 13 of the measuring device 10 shown in FIG. 1. In this embodiment the chopper 13 comprises two rotating discs 13a and 13b, which are mainly circular. On the edge of each disc 13a and 13b are formed two notches 25 on the opposite edges of the discs. Correspondingly, the notches 25 could also be apertures formed on the edges of the discs 13a and 13b. In FIG. 3 the discs rotate in the same direction and they are positioned so as to partly overlap. The rotational movements of the discs 13a and 13b are synchronized with respect to each other so that the notches 25 in the different discs will always meet between the discs. This means that the discs 13a and 13b form a light chopper which is used for cutting the emission light path leading to the measuring detector 11, for the purpose of time-resolved imaging.

To increase the speed of rotation of the discs further, the shutter may be underpressurized. If necessary, the underpressurized space is filled with a small-molecule gas, such as helium, in which case the friction on the discs is low, that is, the friction of the gas molecules against the shutter discs is considerably smaller than it would be if the filler gas used in the underpressurized state was air. With lower friction, the rotational resistance also decreases and the rotating motor is able to rotate the light chopper discs faster and/or more easily, and a fast, silent device is obtained.

In FIG. 3 the chopper 13 discs 13a and 13b are shown in such a position that the discs rotate clockwise and the shutter aperture 26 formed by the notches 25 is about to open.

Figure 4:
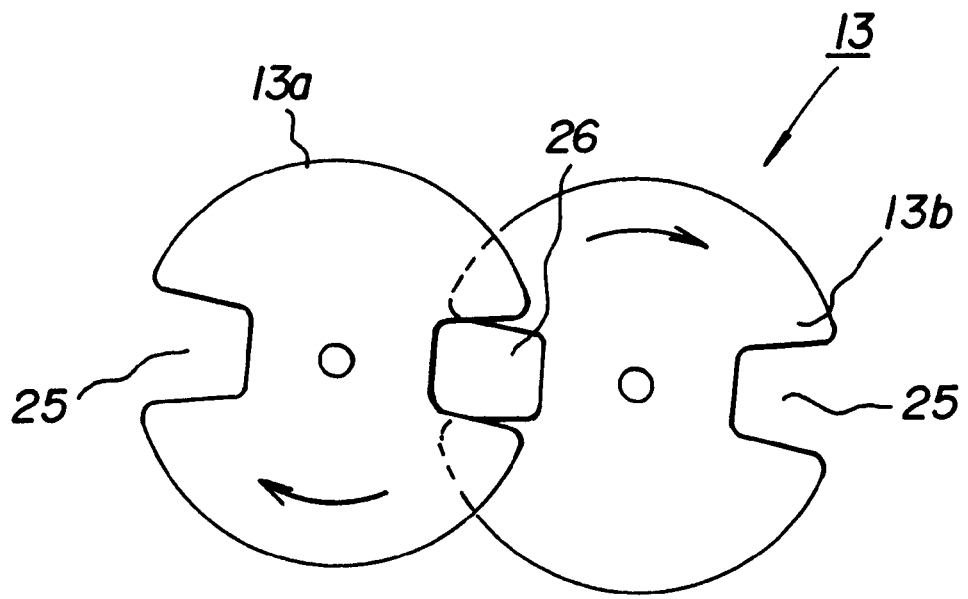

In FIG. 4, on the other hand, the chopper 13 discs 13a and 13b are in such a position that the aperture 26 is already completely open.

In the embodiment shown in FIGS. 3 and 4 the chopper has two discs 13a and 13b and each of them has two notches 25. By means of this structure, the speed of opening of the aperture 26 formed by the notches 25 can be made twice as fast as that of a structure provided with one shutter disc. If necessary, the number of notches 25 in the discs 13a and 13b may be even greater, for example, three or four. With the chopper structure shown, the time differences required in time-resolved fluorescence measurement can be controlled accurately between the flashes of the excitation light and the time of measurement. The chopper 13 in a measuring device 10 is most preferably located between the lens parts 14a and 14b of the emission lens 14. The set of lenses 14ab is comprised of two separate lens groups 14a and 14b, one of which is located on one side of the light chopper and the other on the other side. Between the lens groups 14a and 14b is the optical aperture plane of the set of lenses 14ab. The light chopper is positioned between these sets of lenses 14a and 14b, on the aperture plane.

Figure 5:
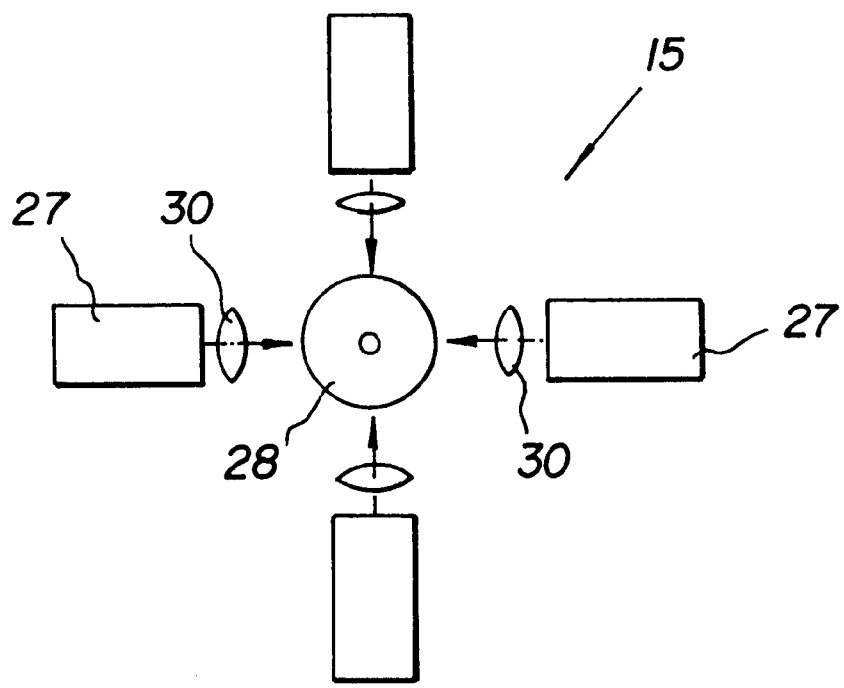

FIG. 5 shows diagrammatically an example of an embodiment of a light source 15 which comprises four flash lamps 27, each of which is also equipped with a condensing lens 30. In the centre of the flash lamps 27 there is a mirror 28 which is inclined at an angle of 45° with respect to the vertical plane, as shown in FIG. 1. FIG. 1 also shows that the mirror 28 is provided with a rotating motor 29. When the mirror 28 is rotated, it is alternately in each light path leading from the flash lamp 27 while it rotates. In such a case the said flash lamp is triggered electrically, which means that the light pulse, that is, the illuminating beam of short duration which is emitted from the lamp, travels via the mirror surface of the rotating mirror, through the filter 18 and the excitation light objective 19 to the mirrors 21 and 22 or the mirrors 23 and 24, finally reaching the sample. The triggering of a single flash lamp is such a rapid occurrence that the rotating mirror has time to rotate only very little (by a fraction of the angular degree) during the duration of the light pulse emitted from the lamp, and thus this illuminating beam of short duration but high intensity has ample time to be reflected forward from the mirror surface of the rotating mirror.

Figure 6:
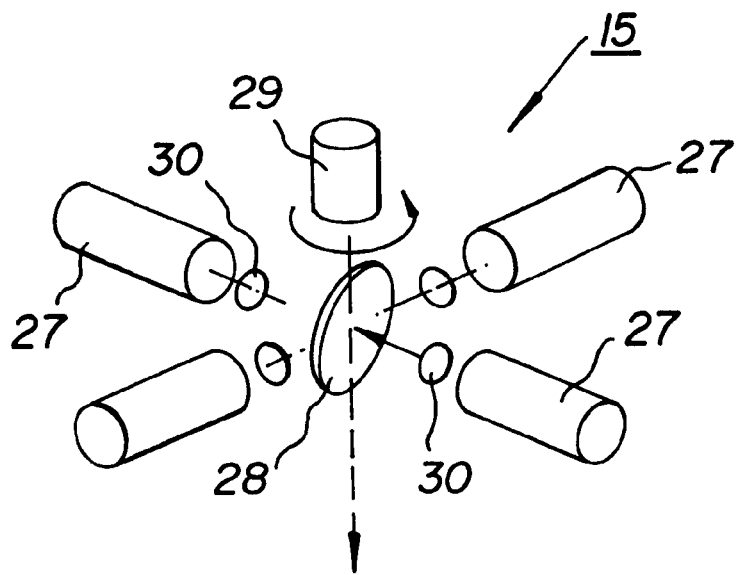

FIG. 6 shows axonometrically the positioning of the lamps 27, condensing lenses 30 and the mirror 28 with respect to each other when using four lamps.

Figures 7, 8:
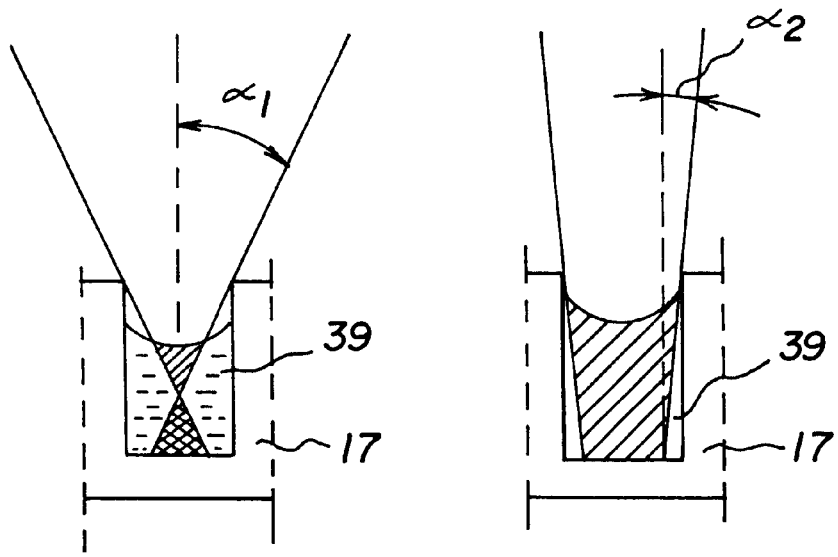

FIG. 7 shows a diagrammatic section of a sample well in a known device. The figure shows that the light beams enter the sample well 39 of the sample plate 17 at a relatively wide angle $\alpha_1$. This means that the sample wells at different points of the sample plate receive different amounts of excitation light/illumination light. In FIG. 7, the illuminated area is shown diagrammatically by shading with oblique lines.

In FIG. 8, the beams of light enter the sample well 39 of the sample plate 17 according to the excitation illumination method relating to the invention at the angle $\alpha_2$, which is much smaller than that shown in FIG. 7. This means that the sample wells at different points of the sample plate receive substantially the same amount of excitation light illumination light.

Figure 9:
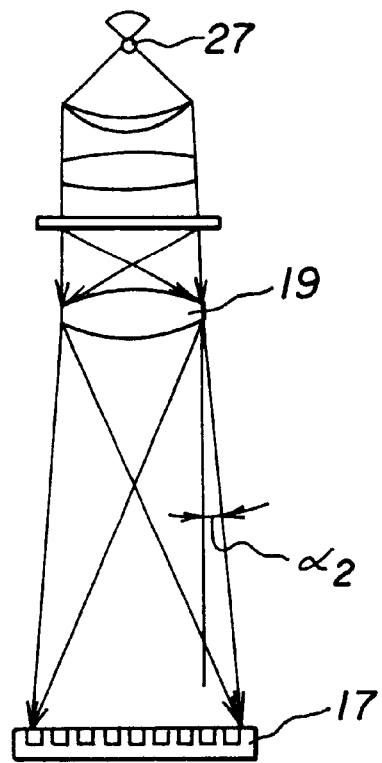
Figure 10:
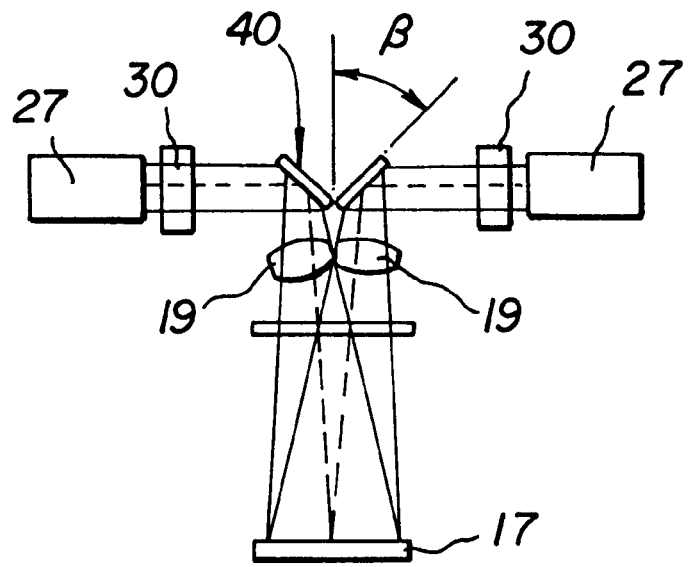

FIG. 9 shows a sample plate excitation illumination system which applies a known manner of illumination. Due to this, the illumination of the sample plate 17 is uniform. The beams of light arrive at the sample plate at a small angle $\alpha_2$ FIG. 10 shows an excitation illumination system which consists of a fixed mirror polyhedron 40 in the centre of the circle. The light from the lamps 27 is directed through the lenses 30 to the mirror polyhedron 40, and from there on to the excitation objectives 19 specific to each lamp, which image the aperture planes of the excitation optics on the sample plate 17.

Figure 11:
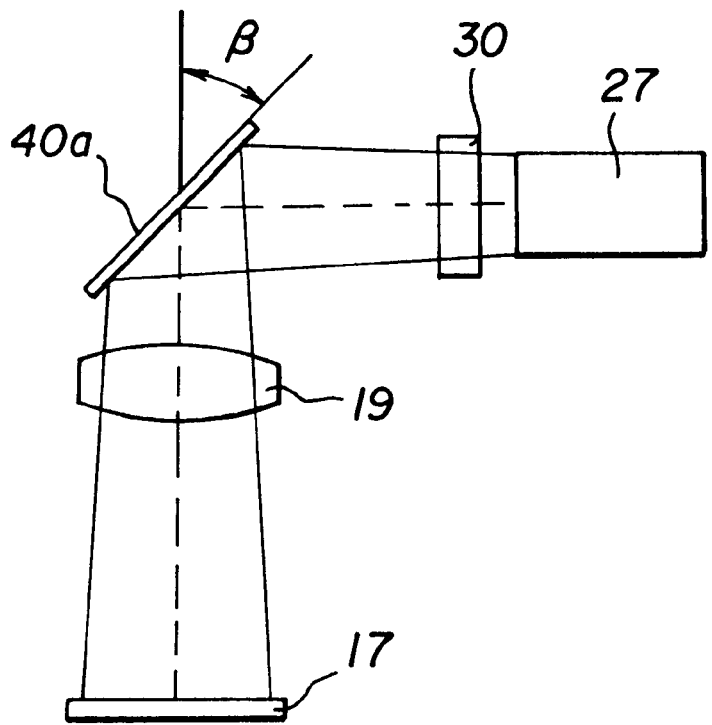

FIG. 11 shows a detail of FIG. 10. The angle of one mirror surface 40a of the mirror polyhedron 40 is slightly over 45 degrees.

Figure 12:
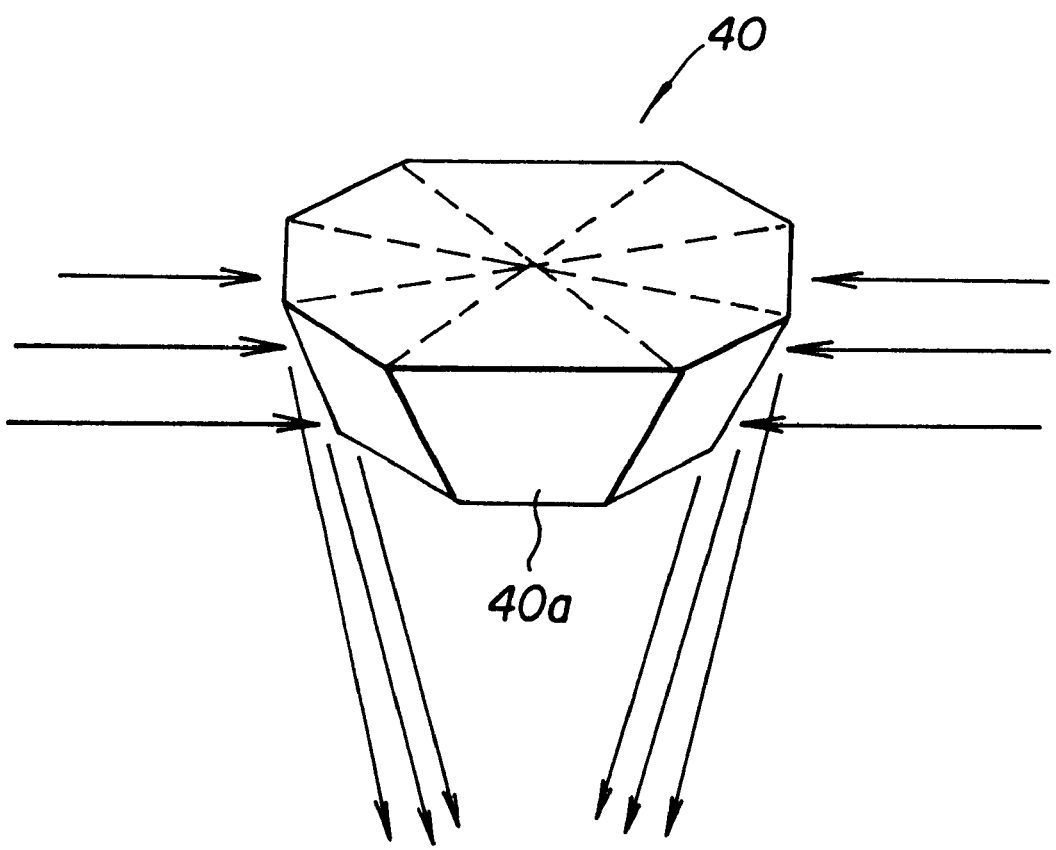

FIG. 12 shows the mirror polyhedron 40 axonometrically.

Figure 13:
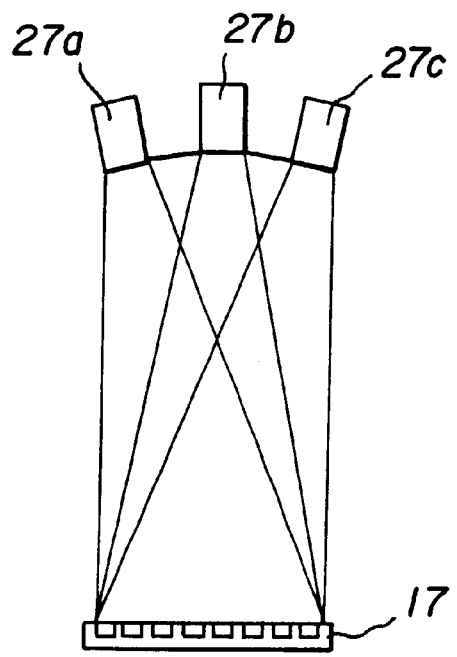

FIG. 13 shows one embodiment for illuminating the sample plate 17. Above the plate 17 are several lamps 27 and their optics positioned adjacent to one another, the lamps being directed towards the sample plate 17.

Figure 14:
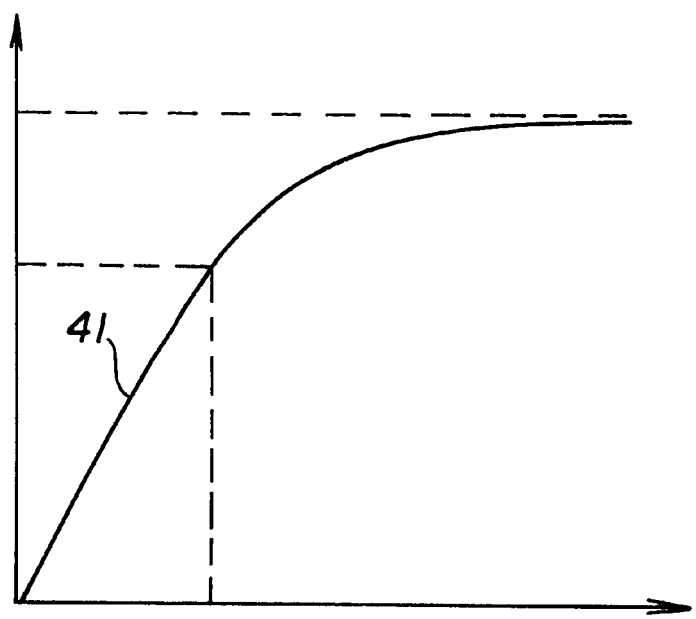

FIG. 14 shows a general fluorescence measuring diagram. With a sufficiently low intensity level of the sample's excitation light is achieved the fact that measurement takes place in the linear measurement area 41.

Figure 15:
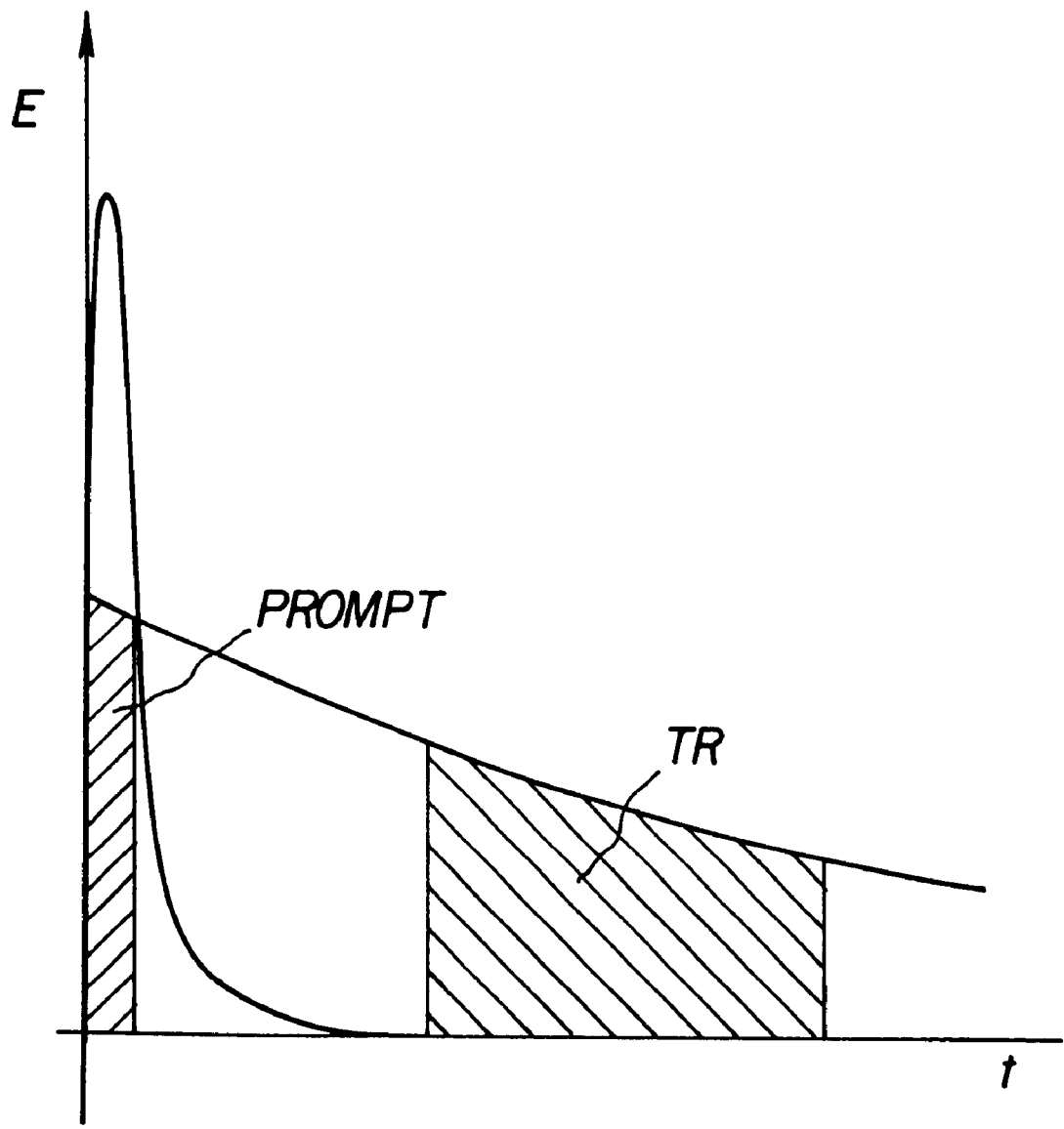

FIG. 15 shows the difference in principle between prompt and TR fluorescence measurements. In the figure it can be seen that the excitation light pulse should be short in order for TR measurement to be successful.

Figure 16:
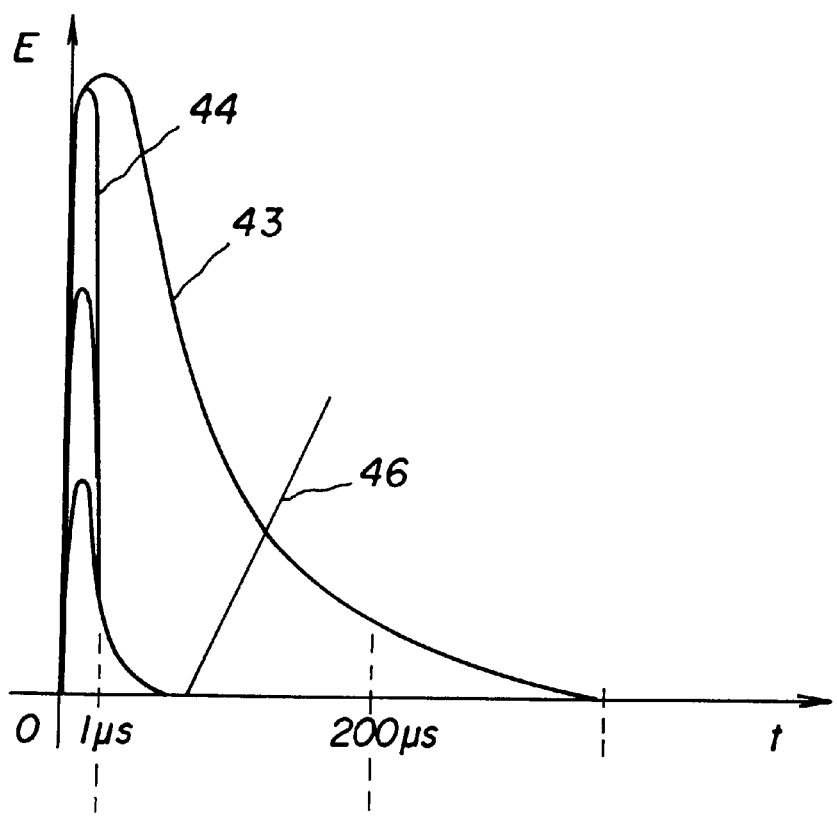

FIG. 16 shows a comparison of the durations of light pulses emitted from different types of flash lamps as a function of time. The lifetime curve 43 of a single powerful lamp is of tong duration. The average pulse 44 obtained with several small lamps is of short duration.

Figure 17:
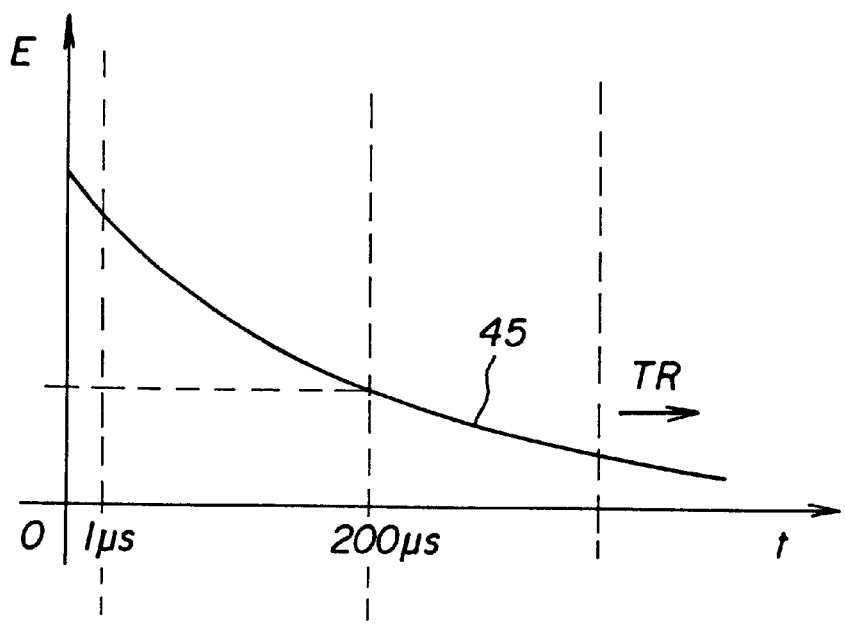

FIG. 17 shows the duration of the fluorescence 45 of a sample. FIG. 17 shows that the fluorescence has already been reduced to a half by the time the light from the powerful lamp has dimmed in FIG. 16. This means that TR fluorescence measurement cannot be carried out efficiently by means of a single powerful flash lamp. FIG. 16 also shows the effect of the tail light chopper 46 placed in front of the lamp for shortening the length of the light pulse. It has, however, been shown in practice that this light chopper does not improve the situation. Despite the chopper, a powerful lamp causes so much background interference that efficient TR measurement cannot be carried out.

EMBODIMENTS

A light source according to a preferred embodiment of the invention comprises two or more flash lamps, and the measuring device comprises a timer for switching the lights on simultaneously or timed in phases as desired. The following advantages are achieved by means of the device relating to the invention:

- a high average pulse power of the light source
- narrow light source pulse width, which is required in certain time-resolved measurements
- optical power guarantees sufficiently short measuring times in fluorescence measurement
- the intervals for changing the light source bulbs are notably long in comparison to a continuous light source
- the structure of the light source is economical in comparison to other light sources with corresponding pulse power
- the same device can be used to carry out absorption measurements of both the UV region and the visible region by imaging on extremely high-density sample plates.

According to a preferred embodiment of the invention, the light source of the measuring device comprises a rotating mirror on the different sides of which the flash lamps are located so that when the mirror rotates, the light beams from the lamps are directed one at a time, and the light beams from all lamps thus once during one rotation of the mirror, via the rotating mirror at the sample, either directly or through other optical means such as mirrors.

The light source of one preferred measuring device comprises eight flash lamps, which are at an angle of 45° with respect to each other, between which lamps a mirror provided with a rotating motor and a vertical rotation axis is placed, the said mirror being inclined at an angle of 45° with respect to the vertical plane.

The frequency of each flash lamp in the light source is, for example, 200 Hz, and they are controlled to flash at an interval of 0.625 ms with respect to each other, so that during a 5 ms period, a total of eight flashes of light are obtained.

In the light source of the measuring device the lamps may also flash simultaneously, in which case the directions of the illuminating beams are controlled by fixed mirror surfaces instead of a rotating mirror. If, therefore, the flash lamps are arranged to flash simultaneously, a rotating mirror is not used, but a fixed mirror system instead.

The measuring device preferably comprises a light chopper, which is synchronized with the timer of the light source. The chopper comprises, for example, at least two rotating discs or the like, on the circumference of which, or its vicinity, there is at least one notch or opening, and which discs are positioned so as to overlap at least partly, so that as the discs rotate, the openings in the adjacent discs form the chopper aperture when they meet at the same point.

In one embodiment the chopper comprises at least two discs rotating in the same direction, the said discs being mainly circular and at least two notches or openings being formed on the edges of both discs, at opposite edges of the discs.

Equipped with the components shown in FIG. 1, the measuring device 10 is a multifunction device, with which, for example, the following assays can be carried out:

In a fluorescence assay, the light emitted from the light source 15, which light is continuous wave light or pulse light, is directed towards the sample 17 through an objective 19 and mirrors 21 and 22. Both a dichroic mirror 22a and a half-transmitting mirror 22b may be used. Fluorescence measurement is carried out by means of a detector 11 and an emission objective 14. If the light source is a flash lamp, the light chopper 18 is in that case permanently in the open position. If, on the other hand, the light source is a continuous wave lamp, an electrically controlled shutter is used in place of the light chopper.

In the example shown in FIG. 1 the light source is comprised of four flash lamps 27, which means that the intensity of the light of the excitation light source 15 is four times greater than with a single lamp. In the example case, the flash lamps 27 are arranged to flash in phases one after the other, in which case the rotating mirror 28 is used to direct the light emitted by the lamps 27 at the sample 17. Directed via the mirror 28, the light beams of all lamps 27 can be directed in turn along the same optical path.

In time-resolved fluorescence measurement the light source 15 is always a pulse mode light source (e.g. a flash lamp), the light emitted from which is directed towards the sample 17 through an excitation objective 19 and mirrors 21 and 22. Depending on the measurement, either a dichroic mirror 22a or a half-transmitting mirror 22b is used. In time-resolved fluorescence measurement, a light chopper 13 and a detector 11 are needed in the emission light path when the detector used is a cooled CCD camera. If, on the other hand, the detector 11 is an Intensified Charge Coupled Device camera, or ICCD camera, a gatable intensified charge coupled device camera is used as a light chopper and no mechanical light chopper is required.

In the example shown in FIG. 1, the optical power of the excitation light source 15 comprising four flash lamps 27, which flash at different phases, can be made four times greater than with a single flash lamp.

By using separate small flash lamps, the excitation illumination period of the measuring device can be determined much more accurately than by using one large lamp, because the illumination time of a small lamp is considerably shorter than that of a large one. The background interference can also be reduced because the "tail" of a single powerful flash lamp is relatively of much longer duration than that of a less powerful flash lamp.

When measuring, that is, imaging luminescence, the mirror unit 22 is not in use, and thus the dichroic mirror 22a or the half-transmitting mirror 22b are not in use. The scattering plate 20 is not in use either. However, filters, a shutter and a dimmer may be in use if necessary.

If, for example, luminescence is measured and there is no light chopper in the device, a solid black plate is used as a camera shutter in place of the filter in the filter wheel, by moving which plate away from the front of the camera and correspondingly to the front of the camera, a shutter-like on-off action can be obtained in the camera.

In a photometric assay the light emitted by the light source 15, which is continuous wave light or pulse light, is directed by means of mirrors 23 and 24 below the sample 17. According to the example shown in FIG. 1, the light source 15 comprises four flash lamps 27 which flash at different phases in order to increase optical power. Photometric measurement is carried out by means of a detector 11 and an emission objective 14.

Absorption measurement is carried out by using visible light from below the sample and by means of a scattering plate 20.

In shadow imaging of UV absorption, the light source 15 is a UV light source, the light emitted by which is directed by means of mirrors 23 and 24 onto the underside of the sample 17. According to the example of an embodiment shown in FIG. 1, the light source 15 comprises four flash lamps 27 which flash at different phases. Since the wavelength range of the light emitted by the flash lamps 27 is wide, UV light can be directed at the sample 17 by means of the filter 18. Above the sample 17 is placed a light wavelength converter plate 20, which converts the ultraviolet light into visible light, the intensity of which is measured by means of a camera and which is proportional to the amount of UV light directed at the converter plate, that is, it is proportional to the absorption of UV light. If necessary, an opal glass may also be positioned below the sample 17. In such a case the shadow imaging of UV absorption is carried out by means of a detector 11 and an emission objective 14.

EXAMPLE 1

The light source 15 of the example of an embodiment shown in FIG. 5 comprises four flash lamps, where the rotational frequency of the rotating mirror is 200 Hz. This means that the interval between two successive pulses of one lamp is 5 ms. According to the invention, the lamps are controlled so that they flash at a 1.25 ms time difference with respect to each other, which means that during one 5 ms period, a total of four flashes of light are obtained. The combined pulse frequency of the lamps achieved with the construction described in the example is in this case 800 Hz. This is four times greater compared with that obtained with a single lamp. By means of this solution the optical power of the light source 15 is quadrupled compared with the optical power obtained with one lamp. When even greater optical power is required, the number of flash lamps can be further increased, for example, to eight flash lamps.

EXAMPLE 2

In the example of an embodiment shown in FIGS. 3 and 4, the speed of rotation of the chopper 13 discs 13a and 13b is 24000 rpm, that is, the rotational frequency is 400 Hz, in other words the wheel rotates at 400 rpm. If the light chopper disc has two apertures 26, it will open 48000 times per minute, that is, 800 times per second. The opening frequency of the apertures is in that case 800 Hz.

Since one flash of light emitted by the flash lamp should correspond to each aperture of the light chopper, the total frequency of the pulse light source should also be 800 Hz. This means that in the example of the embodiment shown in FIGS. 4 and 5, it is advantageous to modify the light source so that it incorporates eight flash lamps flashing at 1.25 ms intervals. The frequency of each individual lamp is 100 Hz, that is, an individual lamp flashes 100 times per second. This means that the rotational frequency of the rotating mirror should be 100 Hz, or 6000 rpm. During one rotation of the mirror, each individual flash lamp is triggered always at 1.25 ms intervals, which means that when the rotation is completed, 8 times 1.25 ms, that is, 10 ms have elapsed, which corresponds to a frequency of 100 Hz. During one rotation in this case eight flashes of light are obtained and the combined pulse frequency of the lamps is 800 Hz. The frequency of a single lamp is still 100 Hz.

One flash of light from the flash lamp occurs during each interval in the opening of the apertures of the light chopper, and during the next interval the next lamp flashes etc. What is essential is the synchronization between the lamps and the camera. In the device relating to the example, one flash occurs between the openings of the apertures. The flash of excitation light takes place, for example, about 10 µs before the aperture begins to open.

EXAMPLE 3

Four apertures in the chopper discs, speed of rotation of chopper discs 24000 rpm, flashing interval 1.25 ms/2=0.625 ms, eight lamps in the light source, speed of rotation of rotating mirror 12000 rpm.

EXAMPLE 4

If the sample plate has 384 wells, the excitation time is 1 s and the time spent for reading the light intensity data on the camera's ccd matrix electronically, that is, the reading time, is 30 s for a full resolution image, then the sample is subjected to 800 excitation light pulses when the overall frequency of the excitation light source is 800 Hz. If the sample plate has 1536 wells and volume of a single well is 5 µl, 8000 excitation light pulses will be required. The measuring time is in this case 10 s and the reading time 30 s. If the volume of the well is 1 µl and there are 1536 wells in the sample plate, 40000 pulses are required, that is, a measuring time of 50 s. A short (reading) time reading, that is, a 2 s fast reading, is also possible in all measurements, but in this case the noise increases, markedly impairing the end result of imaging.

Instead of the mechanical chopper shown in FIGS. 3 and 4, a liquid crystal shutter device, or LCD, can also be used. It is, however, slower and its light dimming capacity is not sufficient for all applications, but it may allow light to pass through, which means that the proportion of the disturbing background signals of the number of detectable signals increases. Another disadvantage is its sensitivity to temperature, since the wavelength band of the light passing through is dependent on the temperature of the component.

The cooled CCD camera (c-CCD) and the light chopper can be replaced by an Intensified Charge Coupled Device, or ICCD camera. Its resolution is, however, poorer and its dynamics inferior to those of a c-CCD camera.

On the aperture plane, that is at the location of the chopper, a dimmer and shutter may also be substituted for it.

The chopper 13 discs 13a and 13b may also be stopped at exactly the desired point, which means that the chopper is suitable for luminescence measurement.

EXAMPLE 5

If the excitation light power is a 0.2 J/pulse, then at a flash frequency of 100 Hz of one lamp, an average power of 20 W is obtained for one lamp. If there are eight lamps in the device, the average power is 160 W.

EXAMPLE 6

The chopper disc has four apertures and there are eight flash lamps in the lamp unit. When the lamps are triggered, 0.2 joules of energy are supplied to each one in turn. This means that the frequency of each individual lamp is 200 Hz, in other words the overall frequency of the entire lamp system is 1600 Hz, which means that an average output of 320 W is obtained with the lamp unit.

Depending on type, the service life of an arc lamp is typically about 300–1000 h, which means a maximum of about 40 days' use, after which the lamp has to be changed. After the said period of use, the intensity of the lamp has decreased to about a half, and at the same time the inner surface of the globe of the lamp has typically become covered in metal detached from the electrodes and other impurities. A lamp which has become cloudy on its inner surface will heat up more than its normal use would require and may even cause a risk of explosion of the lamp if the lamp is not changed in time. This is due to the fact that while arc lamps are switched on, there is considerable overpressure inside them, which rises the hotter the temperature at which the lamp has to operate as it ages, and this causes the risk of explosion. With flash lamps, on the other hand, there is no such direct risk, or it is at least substantially less, because when a flash lamp is switched on, its pressure is substantially lower than that of an equally powerful arc lamp and may even be close to normal air pressure.

In the device relating to the invention, the highest power permitted for the flash lamps used is 0.5 J. The lamp may, however, be used at a lower voltage, which lengthens its service life considerably. This gives it a service life which is many times longer than that of an arc lamp. The same output is obtained from the lamps, but the changing interval is prolonged. This means longer service intervals. Another advantage of the device is that even if one or more lamps blow, this does not mean that measurement is discontinued. The blown lamp is detected by power measurement and compensated for by the programme, which means that the measuring device will still function well.

The device relating to the invention makes it possible to obtain an excitation light distribution that is uniform in intensity and applicable to the fluorescence measurement of macro-size sample plates, which distribution it has previously been difficult to achieve while striving to keep the duration of measurement within reasonable limits.

It is obvious to a person skilled in the art that the different embodiments of the invention may vary within the limits of the claims presented below.

What is claimed is:

1. An imaging device for biochemical or medical samples, said device comprising
    a holder for objects to be imaged, which are sample matrices, gels or biological sections,
    two or more pulse mode light sources which are situated on the circumference of a circle for illuminating and/or exciting the objects to be imaged,
    a rotatable mirror in an inclined position located principally in the center of said circle for reflecting the light emitted by each pulse mode light source principally along the same optical path from the mirror to the objects to be imaged,
    means for directing light emitted by said two or more pulse light sources at said rotatable mirror,
    a detector for measuring the objects to be imaged,
    means for directing light from the objects to be measured at the detector, and
    means for switching the flash lamps on successively in phases.

2. An imaging device as claimed in claim 1, wherein
    said two or more pulse light sources are provided with condensing lenses,
    each of said two or more pulse light sources incorporates a triggering device for switching the light sources on alternately at the desired moment by phasing,
    the switching-on frequency of each of said two or more pulse light sources corresponds to the speed of rotation of the rotatable mirror,
    and each of said two or more pulse light sources is adapted to be switched on at the exact moment when the rotatable mirror is at that light source so that the illuminating beam emitted from the light source when it is switched on strikes the reflecting surface of the rotatable mirror and is reflected on towards the objects to be imaged.

3. An imaging device as claimed in claim 1, wherein
    the rotatable mirror is arranged to rotate at 6000 rpm, and
    said two or more pulse light sources comprises eight flash lamps, which are arranged to be triggered at 10 ms intervals.

4. An imaging device as claimed in claim 1, wherein
    said two or more pulse light sources comprises eight flash lamps, the nominal power of which is 50 W.

5. An imaging device as claimed in claim 1, wherein said two or more pulse light sources comprises an even number of flash lamps, of which at first only every other lamp is arranged to be triggered in turn, and that the other lamps are arranged to be alternated for triggering in turn as desired.

6. An imaging device as claimed in claim 1, wherein said two or more pulse light sources comprises an odd number of flash lamps, in which case every other lamp is arranged to be triggered while the mirror rotates.

7. An imaging device as claimed in claim 1, wherein the imaging device comprises a tail light chopper which cuts off the illumination path leading from said at least two pulse mode light sources to the objects to be imaged at a predetermined moment so that the duration of the light emitted from each of said at least two pulse mode light sources separately to the sample is of a desirable length, preventing the after-glow of the light sources from disturbing measurement.

8. An imaging device as claimed in claim 7, wherein the tail light chopper of the imaging device is arranged to cut off the light 3–30 $\mu$s after the moment of triggering of each of said at least two pulse mode light sources.

9. An imaging device as claimed in claim 7, wherein the imaging device comprises an emission light chopper, which is synchronized with said at least two pulse mode light sources, the rotatable mirror and the tail light chopper so that they function together in a synchronous manner.

10. An imaging device as claimed in claim 9, wherein the emission light chopper of the imaging device is a mechanical rotating light chopper or a liquid crystal shutter device (LCD).

11. An imaging device as claimed in claim 9, wherein
    the emission light chopper of the imaging device is a mechanical rotating light chopper which comprises at least two rotatable discs, which are mainly circular,
    at least one notch or opening is formed on an edge part of each rotatable disc,
    the discs are arranged to rotate in the same direction and to partly overlap, and
    rotational movements of the discs are synchronized with respect to each other so that, when the discs rotate and the notches in the different discs meet at the same point, the aperture of the light chopper is in the open position.

12. An imaging device as claimed in claim 11, wherein the emission light chopper of the imaging device comprises two rotatable discs on the edges of each of which are two notches.

13. An imaging device as claimed in claim 12, wherein the rotatable discs of the emission light chopper of the imaging device are arranged to rotate at 24000 rpm.

14. An imaging device as claimed in claim 11, wherein the rotatable discs of the emission light chopper of the imaging device are situated in an underpressurized space filled with air or a small-molecule gas.

15. An imaging device as claimed in claim 1, wherein said detector is a cooled CCD camera.

16. An imaging device as claimed in claim 1, wherein the imaging device further comprises a telecentric lens system, on whose optical aperture plane is situated a light chopper synchronized with the rotatable mirror of the light source.

17. An imaging device as claimed in claim 1, wherein the imaging device further comprises a turnable mirror for directing light from said two or more pulse light sources at the objects to be measured from above and/or below.

18. An imaging device as claimed in claim 1, wherein the imaging device further comprises a feedback photodiode and a partly reflecting mirror, which directs some of the light emitted by each of said two or more pulse light sources at the feedback photodiode.

19. An imaging device as claimed in claim 1, wherein the imaging device further comprises an absorption measurement plate, which is a double-acting measurement plate, so that it is simultaneously both a transparent scattering plate which can be used for absorption measurement of visible light and a fluorescent converter plate which can be used for absorption measurement of UV light, and mirrors for directing the light emitted by said two or more pulse mode light sources through the objects to be imaged at the absorption plate.

20. An imaging device as claimed in claim 1, wherein said two or more pulse light sources are flash lamps.

21. An imaging device as claimed in claim 1, wherein said two or more pulse light sources are pulsed lasers.

22. A method for measuring biochemical or medical samples by imaging, according to which method objects to be imaged are illuminated and/or excited by means of two or more flash lamps situated on the circumference of a circle of a pulse mode light source, the flash lamps of the pulse mode light source are switched on successively in phases, light beams emitted by the flash lamps are directed at a rotatable mirror located principally in the center of the circle in an inclined position, light beams reflected from the rotatable mirror are directed principally along the same optical path to the objects to be imaged, and the illumination of the objects to be imaged is used as excitation light by means of which a fluorescence phenomenon is produced in the objects to be imaged, emission light resulting from the phenomenon being measured at different points of the objects to be imaged by means of a detector, or by means of the light passing through the objects to be imaged, the amount of reflection, scattering or absorption obtained through the illumination of the object is measured at different points of the objects to be imaged.

* * * * *